US010863811B2

(12) United States Patent
Parris et al.

(10) Patent No.: US 10,863,811 B2
(45) Date of Patent: Dec. 15, 2020

(54) PROCESS FOR TREATING KERATIN FIBRES WITH INPUT OF HEAT

(75) Inventors: Eric Parris, Sannois (FR); Gabin Vic, Semoy (FR)

(73) Assignee: L'OREAL, Paris (FR)

( * ) Notice: Subject to any disclaimer, the term of this patent is extended or adjusted under 35 U.S.C. 154(b) by 391 days.

(21) Appl. No.: 14/128,097

(22) PCT Filed: Jun. 25, 2012

(86) PCT No.: PCT/EP2012/062223
§ 371 (c)(1),
(2), (4) Date: May 5, 2014

(87) PCT Pub. No.: WO2012/175734
PCT Pub. Date: Dec. 27, 2012

(65) Prior Publication Data
US 2014/0230842 A1    Aug. 21, 2014

Related U.S. Application Data

(60) Provisional application No. 61/510,048, filed on Jul. 20, 2011.

(30) Foreign Application Priority Data

Jun. 23, 2011    (FR) ..................... 11 55575

(51) Int. Cl.
*A45D 7/06*    (2006.01)
*A61K 8/891*    (2006.01)
(Continued)

(52) U.S. Cl.
CPC ................. *A45D 7/06* (2013.01); *A45D 1/04* (2013.01); *A45D 19/0008* (2013.01);
(Continued)

(58) Field of Classification Search
CPC ............ A45D 19/0008; A45D 19/0016; A45D 19/0025; A45D 19/16; A45D 2/367;
(Continued)

(56) References Cited

U.S. PATENT DOCUMENTS 2,263,718 A    11/1941    Cowan
3,941,613 A *   3/1976    Nicoletti ................. 132/270
(Continued)

FOREIGN PATENT DOCUMENTS

DE            2359399 A1    6/1975
DE            3843892 A1    6/1990
(Continued)

OTHER PUBLICATIONS

Winter, Ruth, "A Consumer's Dictionary of Cosmetic Ingredients", 2005, Three Rieers Press, NY, pp. 721.*
(Continued)

*Primary Examiner* — Jacqueline T Johanas
*Assistant Examiner* — Jennifer Gill
(74) *Attorney, Agent, or Firm* — The Marbury Law Group, PLLC (57) ABSTRACT

A process for treating keratin fibres may include applying a hair treatment composition to the keratin fibres. The composition may comprise at least one of fatty substances, surfactants, polymers with a glass transition temperature (Tg) ranging from about 40° C. to about 150° C., oxidation dye precursors, and direct dyes. The process may also include inserting the keratin fibres into a device comprising two elements that are moveable relative to each other between an open position and a closed position. In the closed position, the two elements may define a substantially leaktight closed space. The process may further include moving the two elements into the closed position to confine the keratin fibres in the closed space, and heating the keratin (Continued)

fibres to a temperature ranging from about 40° C. to about 250° C. while the keratin fibres are confined in the closed space.

20 Claims, 1 Drawing Sheet

(51) Int. Cl.
| | |
|---|---|
| *A61K 8/37* | (2006.01) |
| *A61K 8/34* | (2006.01) |
| *A61Q 5/12* | (2006.01) |
| *A61K 8/31* | (2006.01) |
| *A61Q 5/10* | (2006.01) |
| *A61K 8/41* | (2006.01) |
| *A61K 8/898* | (2006.01) |
| *A61Q 5/06* | (2006.01) |
| *A45D 19/00* | (2006.01) |
| *A45D 19/16* | (2006.01) |
| *A45D 1/04* | (2006.01) |

(52) U.S. Cl.
CPC .............. *A45D 19/16* (2013.01); *A61K 8/31* (2013.01); *A61K 8/342* (2013.01); *A61K 8/37* (2013.01); *A61K 8/416* (2013.01); *A61K 8/891* (2013.01); *A61K 8/898* (2013.01); *A61Q 5/065* (2013.01); *A61Q 5/10* (2013.01); *A61Q 5/12* (2013.01); *A45D 2019/0091* (2013.01); *A61K 2800/88* (2013.01)

(58) Field of Classification Search
CPC .... A45D 2019/0066; A45D 2019/0083; A45D 2019/0091
USPC ................ 132/203, 206–208, 229, 269–270
See application file for complete search history.

(56) References Cited

U.S. PATENT DOCUMENTS

| | | | |
|---|---|---|---|
| 4,003,699 A | 1/1977 | Rose et al. | |
| 4,137,180 A | 1/1979 | Naik et al. | |
| RE30,199 E | 1/1980 | Rose et al. | |
| 4,261,375 A * | 4/1981 | Anderson .................... | 132/224 |
| 4,714,820 A * | 12/1987 | Morrison .............. | A45D 2/001 |
| | | | 132/225 |
| 4,743,726 A * | 5/1988 | Hughes et al. ............... | 219/759 |
| 4,849,593 A * | 7/1989 | Hughes et al. ............... | 219/759 |
| 4,874,554 A | 10/1989 | Lange et al. | |
| 4,942,893 A * | 7/1990 | Trottier ............. | A45D 19/0008 |
| | | | 132/208 |
| 5,061,289 A | 10/1991 | Clausen et al. | |
| 5,156,172 A * | 10/1992 | Tancredi .................... | 132/270 |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,706,839 A * | 1/1998 | Patti .............. | 132/277 |
| 5,708,151 A | 1/1998 | Moeckli | |
| 5,766,576 A | 6/1998 | Loewe et al. | |
| 5,933,794 A | 8/1999 | Stalzer | |
| 6,099,592 A | 8/2000 | Vidal et al. | |
| 6,099,593 A | 8/2000 | Terranova et al. | |
| 6,153,178 A | 11/2000 | Lang et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 7,562,661 B2 | 7/2009 | Ueyama et al. | |
| 8,132,576 B1 * | 3/2012 | Trottier .......................... | 132/270 |
| 8,499,770 B2 * | 8/2013 | Smith ........................... | 132/270 |
| 2002/0050013 A1 | 5/2002 | Vidal et al. | |
| 2002/0157682 A1 | 10/2002 | Ueyama et al. | |
| 2003/0019051 A9 | 1/2003 | Vidal et al. | |
| 2004/0129290 A1 * | 7/2004 | Kwan ............................ | 132/270 |
| 2008/0083418 A1 * | 4/2008 | Glenn et al. .................. | 132/208 |
| 2008/0308119 A1 * | 12/2008 | Smith ................ | A45D 19/0008 |
| | | | 132/202 |
| 2009/0211594 A1 * | 8/2009 | Tojo .................... | A45D 19/0008 |
| | | | 132/270 |
| 2010/0263683 A1 * | 10/2010 | Dutheil-Gouret ....... | A61K 8/731 |
| | | | 132/204 |
| 2013/0152959 A1 * | 6/2013 | Genain .................... | A45D 7/06 |
| | | | 132/206 |

FOREIGN PATENT DOCUMENTS

| | | |
|---|---|---|
| DE | 4133957 A1 | 4/1993 |
| DE | 19543988 A1 | 5/1997 |
| EP | 0770375 A1 | 5/1977 |
| EP | 0714954 A2 | 6/1996 |
| EP | 1147762 A2 | 10/2001 |
| EP | 2095737 A1 | 9/2009 |
| FR | 2733749 A1 | 11/1996 |
| FR | 2750048 A1 | 12/1997 |
| FR | 2821250 A1 | 8/2002 |
| FR | 2944438 A1 | 10/2010 |
| GB | 1026978 | 4/1966 |
| GB | 1153196 | 5/1969 |
| JP | 02-019576 | 1/1990 |
| JP | 05-163124 | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | WO 2011151310 * | 12/2011 |

OTHER PUBLICATIONS

Winter, RUth, "A Consumer's Dictionary of Ingredients", 2005, Three Rieers Press, NY, p. 721.*
The International Search Report for corresponding International Patent Application No. PCT/EP2012/062223, dated Nov. 30, 2012.
Todd, Charles, et al., "Volatile Silicone Fluids for Cosmetic Formulations," Cosmetics and Toiletries, vol. 91, Jan. 1976, pp. 27-32.
Porter, M.R., "Handbook of Surfactants," 1991, pp. 116-178.
English Translation of the Office Action for JP 201416385 dated Jul. 3, 2017.
Japanese Patent Application No. H10-231235, filed Feb. 21, 1997, with English Abstract.
Japanese Patent Application No. H-11-509556, filed Aug. 24, 1999, with English Abstract.

* cited by examiner

PROCESS FOR TREATING KERATIN FIBRES WITH INPUT OF HEAT

CROSS REFERENCE TO RELATED APPLICATIONS

This is a national stage application of PCT/EP2012/062223, filed internationally on Jun. 25, 2012, which claims priority to U.S. Provisional Application No. 61/510,048, filed on Jul. 20, 2011, as well as French Application No. FR 1155575 filed on Jun. 23, 2011, the entire contents of each of which is incorporated by reference herein.

BACKGROUND OF THE INVENTION

The invention relates to a process for treating keratin fibres, especially the hair, with input of heat.

In all categories of cosmetic hair products, there is a need for greater performance. Whether in the field of care or dyeing, there is an expectation of a better cosmetic result, greater speed of treatment or an improvement in the remnants of the effects.

In parallel with these needs, it is important to attempt to obtain these effects with lesser amounts of starting materials and with starting materials that are as neutral as possible to reduce the global environmental impact.

There is thus a need for a process that makes it possible to obtain the best performance for a treatment composition in order to afford a higher cosmetic level with an environmental impact that is equal to or less than that which the state of the art proposes today.

BRIEF SUMMARY OF THE INVENTION

Thus, one subject of the invention is a process for treating keratin fibres, in particular the hair, in which:
a hair treatment composition is applied to the keratin fibres, the composition comprising at least one compound chosen from fatty substances, surfactants, polymers with a Tg (glass transition temperature) of between 40 and 150° C., oxidation dye precursors and direct dyes;
the keratin fibres are inserted into a device comprising two elements that are mutually mobile between an open position and a closed position in which the two mobile elements define a substantially leaktight closed space;
the two mobile elements are brought together up to the closed position so as to confine the keratin fibres in the closed space;
the fibres are heated to a temperature of between 40 and 250° C.

A subject of the invention is also a kit comprising:
a device comprising two elements that are mutually mobile between an open position and a closed position in which the two mobile elements define a substantially leaktight closed space, and a heating means;
a compartment containing a composition comprising at least one compound chosen from fatty substances, surfactants, polymers with a Tg of between 40 and 150° C., oxidation dye precursors and direct dyes.

Finally, the invention relates to the use of a device comprising two elements that are mutually mobile between an open position and a closed position in which the two mobile elements define a substantially leaktight closed space and a heating means for treating keratin fibres, and in particular human keratin fibres such as the hair.

BRIEF DESCRIPTION OF THE DRAWINGS

The invention may be better understood on reading the following description of non-limiting implementation examples thereof, and with reference to the attached drawing, in which.

DETAILED DESCRIPTION OF THE INVENTION

For the purposes of the present invention, the expression "substantially leaktight closed space" means that this space allows little or no liquid or gas to pass during the heating step, the space being obturated between the two mobile elements.

In the closed position, both mobile elements are shaped to define a substantially leaktight closed space when the volume of keratinous fibers is arranged in this space. Keratinous fibers can be then partially pinched between both mobile elements, in particular by one or several seals provided on the one or both mobile elements, defining at least partly the periphery of the closed space.

The application of a composition to the hair combined with a step of heating the composition on the hair by supplying heat in a confined manner, especially into an occluded space, allows evaporation of part of the composition by creating a slight excess pressure inside the closed space.

The deposition of the compounds of the composition onto the hair and/or the penetration of these compounds into the hair are thus greatly increased when compared with the application of an identical composition at room temperature. The remnants to shampooing of the deposits and of the resulting cosmetic properties are also increased.

According to one particular embodiment of the invention, the composition comprises at least one compound whose softening point or melting point is between 40 and 150° C. Preferably, the compound has a softening point or melting point of between 50 and 100° C. and even more preferentially between 60 and 90° C.

The softening point or melting point values may be determined by the DSC (differential scanning calorimetry) method; the softening point or melting point then corresponds to the melting peak and the temperature increase is 5 or 10° C./min.

The expression "at least one" is equivalent to the expression "one or more".

According to one particular embodiment, the composition comprises at least one fatty substance.

For the purpose of the present invention, the term "fatty substance" is intended to mean an organic compound which is insoluble in water at normal temperature (25° C.) and at atmospheric pressure (760 mmHg, i.e. $1.013 \times 10^5$ Pa), that is to say with a solubility of less than 4% by weight, preferably of less than 1% by weight and even more preferentially of less than 0.1% by weight. They have in their structure at least one hydrocarbon-based chain comprising at least 6 carbon atoms or a sequence of at least two siloxane groups. In addition, the fatty substances are soluble in organic solvents under the same temperature and pressure conditions, for instance chloroform, ethanol or benzene.

The fatty substances of the invention may be liquid or non-liquid at room temperature (25° C.) and at atmospheric pressure (760 mmHg; i.e. $1.013 \times 10^5$ Pa).

The liquid fatty substances of the invention preferably have a viscosity of less than or equal to 2 Pa·s, better still less than or equal to 1 Pa·s and even better still less than or equal to 0.1 Pa·s at a temperature of 25° C. and at a shear rate of 1 s$^{-1}$.

Liquid fatty substances that may be mentioned include silicone or non-silicone oils.

The term "non-silicone oil" means an oil not containing any silicon atoms (Si) and the term "silicone oil" means an oil containing at least one silicon atom.

More particularly, the fatty substances may be chosen from $C_6$-$C_{16}$ alkanes, non-silicone oils of animal, plant, mineral or synthetic origin, fatty acids, fatty alcohols, esters of a fatty acid and/or of a fatty alcohol, non-silicone waxes of natural or synthetic origin, and silicones.

The fatty alcohols, esters and acids more particularly have at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ alkanes, they are linear or branched, and possibly cyclic. Examples that may be mentioned include hexane, dodecane and isoparaffins such as isohexadecane and isodecane.

As oils of animal, plant, mineral or synthetic origin that may be used, examples that may be mentioned include:

hydrocarbon-based oils of animal origin, such as perhydrosqualene;

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil;

linear or branched hydrocarbons of mineral or synthetic origin, containing more than 16 carbon atoms, such as liquid paraffins, petroleum jelly, liquid petroleum jelly, polydecenes, and hydrogenated polyisobutene such as Parleam®;

fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052® by the company 3M.

The fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The fatty acids that are suitable for use in the invention are more particularly chosen from linear or branched, saturated or unsaturated acids comprising from 6 to 30 carbon atoms and preferably from 8 to 30 carbon atoms. Examples that may be mentioned include lauric acid, palmitic acid and oleic acid.

As regards the esters of fatty acids and/or of fatty alcohols, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$$C_{22}$ fatty acids. The term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be selected especially from the group containing the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate. Examples of esters or mixtures of esters of sugar and of fatty acid that may also be mentioned include:
- the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% diester-triester-polyester;
- the sucrose monopalmitostearate-dipalmitostearate sold by the company Goldschmidt under the name Tegosoft® PSE.

The non-silicone wax(es) are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy raw materials that can be used according to the invention are in particular marine waxes, such as that sold by Sophim under the reference M82, polyethylene waxes or polyolefin waxes in general.

The silicones that may be used in the cosmetic compositions of the present invention are volatile or non-volatile, cyclic, linear or branched silicones, which are unmodified or modified with organic groups, having a viscosity of $5 \times 10^{-6}$ to 2.5 m²/s at 25° C., and preferably $1 \times 10^{-5}$ to 1 m²/s.

The silicones that can be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and more particularly still from:
(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;
(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics.*

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to ASTM standard 445 Appendix C.

Among these polydialkylsiloxanes, mention may be made, in a nonlimiting manner, of the following commercial products:
- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200 with a viscosity of 60 000 mm²/s;
- the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

The silicone gums that can be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:
the mixtures formed from a hydroxy-terminated polydimethylsiloxane or dimethiconol (CTFA), and from a cyclic polydimethylsiloxane, also known as cyclomethicone (CTFA), such as the product Q2 1401 sold by Dow Corning;
mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
mixtures of two PDMSs with different viscosities, and more particularly of a PDMS gum and a PDMS oil, such as the product SF 1236 from the company General Electric. The product SF 1236 is a mixture of a gum SE 30 defined above, with a viscosity of 20 $m^2/s$ and of an oil SF 96 with a viscosity of $5 \times 10^{-6}$ $m^2/s$. This product preferably comprises 15% of gum SE 30 and 85% of an oil SF 96.

The organopolysiloxane resins that can be used in accordance with the invention are crosslinked siloxane systems containing the following units: $R_2SiO_{2/2}$, $R_3SiO_{1/2}$, $RSiO_{3/2}$ and $SiO_{412}$,
in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold especially under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based group. Besides the silicones described above, the organomodified silicones may be polydiarylsiloxanes, in particular polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1 \times 10^{-5}$ to $5 \times 10^{-2}$ $m^2/s$ at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:
polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
alkoxy groups such as the product sold under the name Silicone Copolymer F-755 by SWS Silicones, and Abil Wax® 2428, 2434 and 2440 by the company Goldschmidt.

Preferably, the fatty substance may be chosen from fatty alcohols, fatty acids, non-silicone waxes of natural or synthetic origin, and silicone gums, or mixtures thereof.

The composition may comprise one or more surfactants. The surfactant may be cationic, nonionic, anionic, amphoteric and/or zwitterionic.

The cationic surfactant(s) that may be used comprise, for example, salts of optionally polyoxyalkylenated primary, secondary or tertiary fatty amines, quaternary ammonium salts, and mixtures thereof.

Examples of quaternary ammonium salts that may especially be mentioned include:
those corresponding to the following general formula (I):

in which the groups R8 to R11, which may be identical or different, represent a linear or branched aliphatic group comprising from 1 to 30 carbon atoms or an aromatic group such as aryl or alkylaryl, at least one of the groups R8 to R11 comprising from 8 to 30 carbon atoms and preferably from 12 to 24 carbon atoms. The aliphatic groups may comprise heteroatoms such as, in particular, oxygen, nitrogen, sulfur and halogens.

The aliphatic groups are chosen, for example, from C1-C30 alkyl, C1-C30 alkoxy, polyoxy(C2-C6)alkylene, C1-C30 alkylamide, (C12-C22)alkylamido(C2-C6)alkyl, (C12-C22)alkylacetate, C1-C30 hydroxyalkyl, X— is an anionic counterion chosen from halides, phosphates, acetates, lactates, (C1-C4)alkyl sulfates, and (C1-C4)alkyl- or (C1-C4)alkylarylsulfonates.

Preference is given, among the quaternary ammonium salts of formula (I), on the one hand, to tetraalkylammonium chlorides, for instance dialkyldimethylammonium or alkyltrimethylammonium chlorides in which the alkyl group comprises approximately from 12 to 22 carbon atoms, in particular behenyltrimethylammonium chloride, distearyldimethylammonium chloride, cetyltrimethylammonium chloride or benzyldimethylstearylammonium chloride, or also, on the other hand, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by Van Dyk.

quaternary ammonium salts of imidazoline, for instance those of formula (II) below:

in which R12 represents an alkyl or alkenyl group comprising from 8 to 30 carbon atoms, for example fatty acid derivatives of tallow, R13 represents a hydrogen atom, a C1-C4 alkyl group or an alkyl or alkenyl group comprising from 8 to 30 carbon atoms, R14 represents a C1-C4 alkyl group, R15 represents a hydrogen atom or a C1-C4 alkyl group, X— is an anion chosen from the group of halides, phosphates, acetates, lactates, (C1-C4)alkyl sulfates and (C1-C4)alkyl- or (C1-C4)alkylaryl-sulfonates. $R_{12}$ and $R_{13}$ preferably denote a mixture of alkyl or alkenyl groups comprising from 12 to 21 carbon atoms, for example tallow fatty acid derivatives, $R_{14}$ denotes a methyl group, and $R_{15}$ denotes a hydrogen atom. Such a product is, for example, sold under the name Rewoquat® W 75 by the company Rewo, quaternary diammonium or triammonium salts, in particular of formula (III) below:

in which R16 denotes an alkyl group comprising for about 16 to 30 carbon atoms, optionally hydroxylated and/or interrupted with one or more oxygen atoms; R17 is chosen from hydrogen, an alkyl group comprising from 1 to 4 carbon atoms or a group —(CH$_2$)$_3$—N$^+$(R16a)(R17a)(R18a); R16a, R17a, R18a, R18, R19, R20 and R21, which may be identical or different, are chosen from hydrogen and an alkyl group comprising from 1 to 4 carbon atoms, and X$^-$ is an anion chosen from the group of halides, acetates, phosphates, nitrates, (C1-C4)alkyl sulfates and (C1-C4) alkyl- or (C1-C4)alkylaryl-sulfonates, in particular methyl sulfate and ethyl sulfate. Such compounds are, for example, Finquat CT-P, available from the company Finetex (Quaternium 89), and Finquat CT, available from the company Finetex (Quaternium 75);

quaternary ammonium salts containing one or more ester functions, for instance those of formula (IV) below:

in which:
R22 is chosen from C1-C6 alkyl and C1-C6 hydroxyalkyl or dihydroxyalkyl groups;
$R_{23}$ is selected from:
the group linear or branched, saturated or unsaturated C1-C22 hydrocarbon-based groups R27,
a hydrogen atom,
$R_{25}$ is selected from:
the group the groups R29, which are linear or branched, saturated or unsaturated C1-C6 hydrocarbon-based radicals;
a hydrogen atom,
R24, R26 and R28, which may be identical or different, are chosen from linear or branched, saturated or unsaturated C7-C21 hydrocarbon-based groups;
r, s and t, which may be identical or different, are integers ranging from 2 to 6,
r1 and t1, which may be identical or different, are equal to 0 or 1,
r2+r1=2 r and t1+t2=2 t,
y is an integer ranging from 1 to 10,
x and z, which may be identical or different, are integers ranging from 0 to 10,
X$^-$ is a simple or complex organic or inorganic anion,
with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and may have 12 to 22 carbon atoms, or may be short and may have from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

x and z, which may be identical or different, are preferably 0 or 1.

y is advantageously equal to 1.

Preferably, r, s and t, which may be identical or different, equal 2 or 3, and even more particularly are equal to 2.

The anion X— is preferably a halide, preferably chloride, bromide or iodide, a (C1-C4)alkyl sulfate or a (C1-C4)alkyl- or (C1-C4)alkylaryl-sulfonate. However, it is possible to use methanesulfonate, phosphate, nitrate, tosylate, an anion derived from an organic acid, such as acetate or lactate, or any other anion that is compatible with the ammonium containing an ester function.

The anion X— is even more particularly chloride, methyl sulfate or ethyl sulfate. Use is made more particularly, in the composition according to the invention, of the ammonium salts of formula (IV) in which:

R22 denotes a methyl or ethyl group,
x and y are equal to 1,
z is equal to 0 or 1,
r, s and t are equal to 2,
R23 is chosen from:
the group methyl, ethyl or $C_{14}$-$C_{22}$ hydrocarbon-based groups,
a hydrogen atom,
R25 is chosen from:
the group a hydrogen atom,
R24, R26 and R28, which may be identical or different, are chosen from linear or branched, saturated or unsaturated C13-C17 hydrocarbon-based groups, and more particularly from linear or branched, saturated or unsaturated C13-C17 alkyl and alkenyl groups.

The hydrocarbon-based groups are advantageously linear.

Among the compounds of formula (IV), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Examples of mixtures of ammonium salts that may be used include the mixture containing 15% to 30% by weight of acyloxyethyldihydroxyethylmethylammonium methyl sulfate, 45% to 60% of diacyloxyethylhydroxyethylmethylammonium methyl sulfate and 15% to 30% of triacyloxyethylmethylammonium methyl sulfate, the acyl radicals containing from 14 to 18 carbon atoms and originating from palm oil that is optionally partially hydrogenated.

It is also possible to use the ammonium salts containing at least one ester function that are described in patents U.S. Pat. Nos. 4,874,554 and 4,137,180.

Use may also be made of behenoylhydroxypropyltrimethylammonium chloride sold by the company KAO under the name Quartamin BTC 131.

Preferably, the ammonium salts containing at least one ester function contain two ester functions.

Among the cationic surfactants present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Examples of nonionic surfactants that may be used in the composition used according to the invention are described, for example, in the *Handbook of Surfactants* by M. R. Porter, published by Blackie & Son (Glasgow and London), 1991, pp. 116-178. They are especially chosen from alcohols, α-diols and ($C_1$-$C_{20}$)alkylphenols, these compounds being polyethoxylated, polypropoxylated or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally ethoxylated esters of fatty acids and sorbitan, esters of fatty acids and sucrose, polyoxyalkylenated fatty acid esters, optionally alkoxylated alkylpolyglycosides, alkylglucoside esters, derivatives of N-alkylglucamine and of N-acylmethylglucamine, aldobionamides and amine oxides.

The nonionic surfactant(s) that may be used in the composition of the invention are more particularly chosen from:
oxyalkylenated or glycerolated fatty alcohols;
oxyalkylenated alkylphenols, the alkyl chain of which is a C8-C18 alkyl chain;
oxyalkylenated or glycerolated fatty amides;
oxyalkylenated plant oils;
optionally oxyalkylenated C6-C30 acid esters of sorbitan;
optionally oxyalkylenated fatty acid esters of sucrose;
fatty acid esters of polyethylene glycol;
(C6-C30)alkylpolyglycosides;
N—(C6-C30)alkylglucamine derivatives;
amine oxides such as (C10-C14)alkylamine oxides or N-acylaminopropylmorpholine oxides;

copolymers of ethylene oxide and of propylene oxide; mixtures thereof.

More particularly, the mean number of oxyalkylene units is advantageously between 2 and 150 units. preferably, they are oxyethylene or oxypropylene units or mixtures thereof.

As regards the polyglycerolated surfactants, they preferably comprise, on average, from 1 to 20 and in particular from 1.5 to 5 glycerol groups.

Examples of anionic surfactants that may be mentioned include:
- (C6-C30)alkyl sulfates, (C6-C30)alkyl ether sulfates, (C6-C30)alkylamido ether sulfates, alkylaryl polyether sulfates and monoglyceride sulfates;
- (C6-C30)alkylsulfonates, (C6-C30)alkylamidesulfonates, (C6-C30)alkylaryl-sulfonates, α-olefin-sulfonates and paraffin-sulfonates;
- (C6-C30)alkyl phosphates;
- (C6-C30)alkylsulfosuccinates, (C6-C30)alkyl ether sulfosuccinates and (C6-C30)alkylamidesulfosuccinates;
- (C6-C30)alkylsulfoacetates;
- (C6-C24)acylsarcosinates;
- (C6-C24)acylglutamates;
- (C6-C30)alkyl polyglycoside carboxylic ethers; (C6-C30) alkyl polyglycoside sulfosuccinates;
- (C6-C30)alkylsulfosuccinamates;
- (C6-C24)acylisethionates;
- N—(C6-C24)acyltaurates;
- fatty acid salts; coconut oil or hydrogenated coconut oil acid salts;
- (C8-C20)acyl-lactylates;
- (C6-C30)alkyl-D-galactoside uronic acid salts;
- salts of polyoxyalkylenated(C6-C30)alkyl ether carboxylic acids, of polyoxyalkylenated (C6-C30)alkylaryl ether carboxylic acids or of polyoxyalkylenated (C6-C30)alkylamido ether carboxylic acids;
- and mixtures thereof.

The amphoteric or zwitterionic surfactant(s) that may be used may especially be optionally quaternized secondary or tertiary aliphatic amine derivatives, in which the aliphatic group is a linear or branched chain comprising from 8 to 22 carbon atoms, the said amine derivatives containing at least one anionic group, for instance a carboxylate, sulfonate, sulfate, phosphate or phosphonate group.

Mention may be made in particular of (C8-C20)alkylbetaines, sulfobetaines, (C8-C20)alkylamido(C3-C8)alkylbetaines and (C8-C20)alkylamido(C6-C8)alkylsulfobetaines.

Among the optionally quaternized secondary or tertiary aliphatic amine derivatives that can be used, as defined above, mention may also be made of the compounds of respective structures (A1) and (A2):

in which formula (A1):
Ra represents a C10-C30 alkyl or alkenyl group derived from an acid Ra-COOH preferably present in hydrolysed coconut oil, or a heptyl, nonyl or undecyl group;
$R_b$ represents a β-hydroxyethyl group; and
$M^+$ represents a carboxymethyl group;
$M^+$ represents a cationic counterion derived from an alkali metal or alkaline-earth metal, such as sodium, an ammonium ion or an ion derived from an organic amine, and
$X^-$ represents an organic or inorganic anionic counterion, such as that chosen from halides, acetates, phosphates, nitrates, $(C_1-C_4)$alkyl sulfates, $(C_1-C_4)$alkyl- or $(C_1-C_4)$ alkylarylsulfonates, in particular methyl sulfate and ethyl sulfate; or alternatively $M^+$ and $X^-$ are absent;

in which formula (A2):
B represents the group —CH2-CH2-O—X';
B' represents the group —(CH2)zY', with z=1 or 2;
X' represents the group —CH$_2$—C(O)OH, —CH$_2$—C(O) OZ', —CH$_2$—CH$_2$—C(O)OH, —CH$_2$—CH$_2$—C(O) OZ', or a hydrogen atom;
Y' represents the group —C(O)OH, —C(O)OZ', —CH2-CH(OH)—SO3H or the group —CH2-CH(OH)—SO3-Z';
Z' represents a cationic counterion derived from an alkali metal or alkaline-earth metal, such as sodium, an ammonium ion or an ion derived from an organic amine;
$R_{a'}$ represents a C10-C30 alkyl or alkenyl group of an acid Ra'-C(O)OH preferably present in coconut oil or in hydrolysed linseed oil, an alkyl group, especially of C17 and its iso form, or an unsaturated C17 group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of $(C_8-C_{20})$alkylbetaines such as cocobetaine, and $(C_8-C_{20})$alkylamido$(C_3-C_8)$alkylbetaines such as cocamidopropylbetaine, and mixtures thereof. More preferentially, the amphoteric or zwitterionic surfactant(s) are chosen from cocamidopropylbetaine and cocobetaine.

According to another embodiment, the composition comprises at least one polymer whose glass transition temperature (Tg) is between 40 and 150° C.

The polymers with a Tg of between 40 and 150° C. may be chosen from homopolymers and copolymers, which are especially in block and/or random form, such as polyacrylics, polymethacrylics, for instance polyacrylamides or polymethacrylic acids, polyolefins, polystyrenes, poly(vinyl halides), for instance PVC (polyvinyl chloride), poly(vinyl nitriles), polyurethanes, polyesters, polyvinylics, polyvinyl esters, polycarbonates, polysulfones, polysulfonamides, polycyclics containing a ring in the main chain, for instance polyphenylenes, polymers containing a heteroatom in the main chain, for instance polyamides, or polyoxyphenylenes.

In the case of homopolymers, they may be chosen more particularly from homopolymers consisting of the following monomers:

The monomers whose homopolymers have glass transition temperatures of greater than or equal to 40° C. are chosen, preferably, from the following monomers:
the methacrylates of formula $CH_2=C(CH_3)$—COOR1, in which R1 represents a linear or branched alkyl group containing from 1 to 4 carbon atoms, such as a methyl, ethyl, propyl or isobutyl group, the said alkyl group also possibly being substituted with one or more substituents chosen from hydroxyl groups and halogen atoms (Cl, Br, I or F), or R1 represents a C4 to C12 cycloalkyl group, the acrylates of formula CH$_2$=CH—COOR2
in which R2 represents a C4 to C12 cycloalkyl group such as isobornyl acrylate or a tert-butyl group,
the (meth)acrylamides of formula:

in which R7 and R8, which may be identical or different, each represent a hydrogen atom or a linear or branched C1 to C12 alkyl group such as an n-butyl, t-butyl, isopropyl, isohexyl, isooctyl or isononyl group; or R7 represents H and R8 represents a 1,1-dimethyl-3-oxobutyl group, and
and R' denotes H or methyl. Examples of monomers that may be mentioned include N-butylacrylamide, N-t-butylacrylamide, N-isopropylacrylamide, N,N-dimethylacrylamide and N,N-dibutylacrylamide, styrene and derivatives thereof such as chlorostyrene, and mixtures thereof.

Monomers that are particularly preferred are methyl methacrylate, isobutyl methacrylate, isobornyl (meth)acrylate, trifluoroethyl methacrylate and styrene, and mixtures thereof.

Measurement of the glass transition temperature (Tg) of the polymer may be performed according to various methods; for example, it is performed by DMTA (dynamic and mechanical temperature analysis), by DTA (differential thermal analysis) or by DSC (differential scanning calorimetry). The measurement by DSC may be performed according to standard ASTM D 3418-97.

According to another embodiment, the composition comprises an oxidation dye precursor or a direct dye.

The oxidation dyes may be oxidation bases or couplers.

Among the oxidation bases, mention will be made in particular of ortho- or para-phenylenediamines, ortho- or para-aminophenols, and heterocyclic compounds such as pyridine, pyrimidine or pyrazole derivatives.

Among the couplers, also known as colour modifiers, mention may be made of aromatic meta-diamines, meta-aminophenols, meta-diphenols and heterocyclic couplers.

Among the para-phenylenediamines, examples that may be mentioned more particularly include para-phenylenediamine, para-tolylenediamine, 2--chloro-para-phenylenediamine, 2,3-dimethyl-para-phenylenediamine, 2,6--dimethyl-para-phenylenediamine, 2,6-diethyl-para-phenylenediamine, 2,5--dimethyl-para-phenylenediamine, N,N-dimethyl-para-phenylenediamine, N,N-diethyl-para-phenylenediamine, N,N-dipropyl-para-phenylenediamine, 4-amino-N,N--diethyl-3-methylaniline, N,N-bis(β-hydroxyethyl)-para-phenylenediamine, 4-N,N-bis(β-hydroxyethyl) amino-2-methylaniline, 4-N,N--bis-(β-hydroxyethyl) amino-2-chloroaniline, 2-β-hydroxyethyl-para-phenylenediamine, 2--fluoro-para-phenylenediamine, 2--isopropyl-para-phenylenediamine, N-(β-hydroxypropyl)-para-phenylenediamine, 2--hydroxymethyl-para-phenylenediamine, N,N--dimethyl-3-methyl-para-phenylenediamine, N-ethyl-N--(β-hydroxyethyl)-para-phenylenediamine, N-(β,γ-dihydroxypropyl)-para-phenylenediamine, N--(4'--aminophenyl)-para-phenylenediamine, N-phenyl-para-phenylenediamine, 2-β--hydroxyethyloxy-para-phenylenediamine, 2β-acetylaminoethyloxy-para-phenylenediamine and N--(β-methoxyethyl)-para-phenylenediamine, and the addition salts thereof with an acid.

Among the para-phenylenediamines mentioned above, para-phenylenediamine, para-tolylenediamine, 2--isopropyl-para-phenylenediamine, 2β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3--dimethyl-para-phenylenediamine, N,N-bis(β-hydroxyethyl)-para-phenylenediamine, 2--chloro-para-phenylenediamine and 2-β-acetylaminoethyloxy-para-phenylenediamine, and the addition salts thereof with an acid, are most particularly preferred.

Among the bis(phenyl)alkylenediamines, examples that may be mentioned more particularly include N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(-hydroxyethylaminomethyl)phenol and 4-amino-2-fluorophenol, and the addition salts thereof with an acid.

Among the ortho-aminophenols that may be mentioned more particularly, for example, are 2-aminophenol, 2-amino-5-methylphenol, 2-amino-6-methylphenol and 5-acetamido-2-aminophenol, and their addition salts with an acid.

Among the pyridine derivatives that may be mentioned more particularly are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives that may be mentioned more particularly are the compounds described, for example, in patents DE 2 359 399; JP 88-169 571; JP 05 163 124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,—N7,N7-tetramethylpyrazolo[1,5-a]pyrimidine-3,7-diamine and 3-amino-5-methyl-7-imidazolylpropylaminopyrazolo[1,5- a]pyrimidine, and the addition salts thereof with an acid, and the tautomeric forms thereof, when a tautomeric equilibrium exists.

Among the pyrazole derivatives that may be mentioned more particularly are the compounds described in patents DE 3 843 892 and DE 4 133 957 and patent applications WO 94/08969, WO 94/08970, FR-A-2 733 749 and DE 195 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

The oxidation bases generally represent from 0.0005% to 12% by weight approximately, and even more preferentially from 0.005% to 6% by weight approximately, relative to the total weight of the dye composition.

The couplers that may be used may be chosen from meta-phenylenediamines, meta-aminophenols, meta-diphenols, naphthols and heterocyclic couplers, for instance indole derivatives, indoline derivatives, pyridine derivatives, indazole derivatives, pyrazolo[1,5 b]-1,2,4 triazole derivatives, pyrazolo[3,2c]-1,2,4 triazole derivatives, benzimidazole derivatives, benzothiazole derivatives, benzoxazole derivatives, 1,3 benzodioxole derivatives and pyrazolones, and the addition salts thereof with an acid.

These couplers are more particularly chosen from 2 methyl-5 aminophenol, 5N-(62-hydroxyethyl)amino-2 methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2 amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 6-hydroxybenzomorpholine, 3,5-diamino-2,6-dimethoxypyridine, 1N-(β-hydroxyethyl)amino-3,4-methylenedioxybenzene, 2,6-bis(β-hydroxyethylamino) toluene, 2,6-dihydroxy-4-methylpyridine, 1H-3-methylpyrazol-5-one and 1-phenyl-3 methylpyrazol-5-one, and the addition salts thereof with an acid.

The direct dyes that may be used may be synthetic or natural, and nonionic, anionic or cationic.

Generally, these direct dyes are chosen from nitrobenzene dyes and azo, anthraquinone, naphthoquinone, benzoquinone, phenothiazine, indigoid, xanthene, phenanthridine, phthalocyanin and triarylmethane-based dyes, alone or as mixtures.

Among the synthetic direct dyes that may be used, mention may be made of azo dyes and especially the cationic azo dyes described in patent applications WO 95/15144, WO 95/01772 and EP 714 954, the content of which forms an integral part of the invention.

Among the azo direct dyes that may also be mentioned are the following dyes, described in the Color Index International, 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made, among these, of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes that may be mentioned are the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone,
1,4-bis(β,γ-dihydroxypropylamino)anthraquinone.

Among the azine synthetic direct dyes, mention may be made of the following dyes: Basic Blue 17, Basic Red 2.

Among the triarylmethane synthetic direct dyes that may be used according to the invention, mention may be made of the following dyes: Basic Green 1, Acid Blue 9, Basic Violet 3, Basic Violet 14, Basic Blue 7, Acid Violet 49, Basic Blue 26, Acid Blue 7.

Among the indoamine synthetic direct dyes that may be used according to the invention, mention may be made of the following dyes:
2-β-hydroxyethlyamino-5-[bis(β-4'-hydroxyethyl)amino] anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinoneimine
3-N-(3'-chloro-4'-methylamino)phenylureido-6-methyl-1,4-benzoquinoneimine;
3-[4'-N-(ethyl,carbamylmethyl)amino]phenylureido-6-methyl-1,4-benzoquinoneimine.

For the purposes of the invention, the term "natural dye" means compounds that exist in nature, whether they have been obtained by extraction or reproduced via chemistry.

Among the natural direct dyes that may be used, mention may be made of ortho-diphenols, lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular henna-based poultices or extracts, may also be used.

The ortho-diphenols that may be used in the process of the invention are in particular:
flavonols, for instance catechin and epicatechin gallate,
flavonols, such as quercetin,
anthocyanidins, for instance cyanidin, delphinidin and petunidin,
anthocyanins or anthocyans, for instance myrtillin,
ortho-hydroxybenzoates, for example gallic acid salts,
flavones, such as luteolin,
hydroxystilbenes, for example tetrahydroxy-3,3',4,5'-stilbene, optionally oxylated (for example glucosylated),
3,4-dihydroxyphenylalanine and derivatives thereof,
2,3-dihydroxyphenylalanine and derivatives thereof, 4,5-dihydroxyphenylalanine and derivatives thereof,
dihydroxycinnamates such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
ortho-polyhydroxyquinones,
ortho-polyhydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins and in particular the proanthocyanidins A1, A2, B1, B2, B3 and C1,
proathocyanins,
tannic acid,
ellagic acid,
and mixtures of the preceding compounds, The composition may also contain other active agents, especially organic acids other than fatty acids, amino acids, sunscreens, ceramides, polymers other than the polymers with a Tg of between 40 and 150° C., organic or mineral thickeners, antioxidants, penetrants, sequestrants, fragrances, buffers, dispersants, film-forming agents, ceramides, preserving agents, stabilizers and opacifiers.

Needless to say, a person skilled in the art will take care to select this or these optional additional compound(s) such that the advantageous properties intrinsically associated with the composition in accordance with the invention are not, or are not substantially, adversely affected by the envisaged addition(s).

Figure 1:
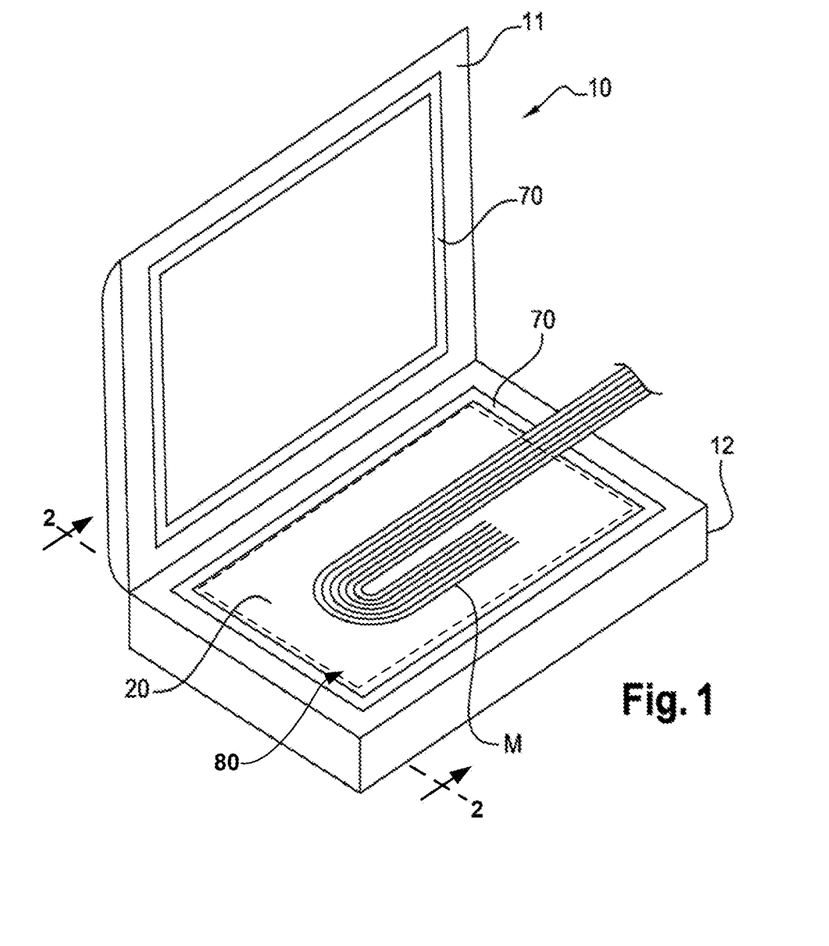
FIG. 1 represents an example of a device according to the invention in the open position.
Figure 2:
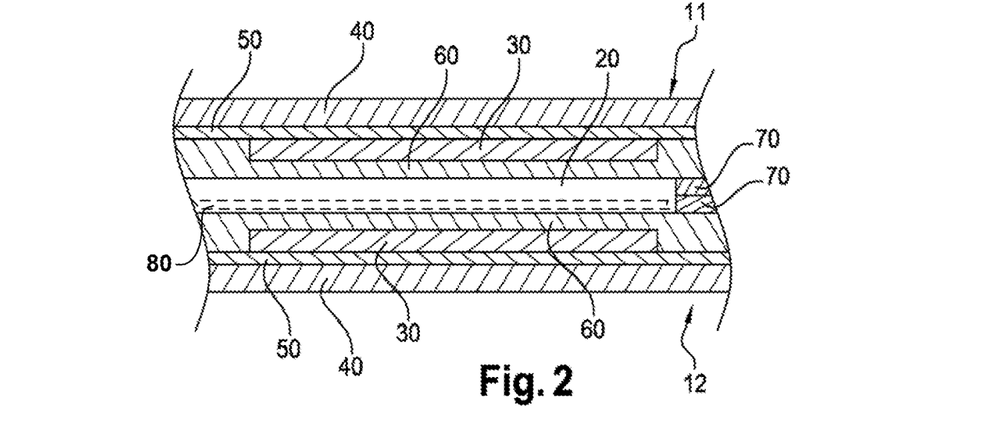
FIG. 2 shows, in partial schematic cross section, the device of FIG. 1, in the closed position.

The treatment according to the invention is performed by applying a hair treatment composition to a lock of hair and by confining the composition on the lock with heating, using a device 10 according to the invention.

More particularly, the process of the invention consists in applying the hair treatment composition described previously onto one or more locks of hair, and then in inserting these locks into the device 10 comprising two elements 11 and 12 that are mutually mobile between an open position and a closed position in which the two mobile elements define a substantially leaktight closed space. The process then consists in bringing the two mobile elements together up to the closed position so as to confine the keratin fibres in the closed space 20; and then in heating the locks to a temperature of between 40 and 250° C. and preferably between 50 and 150° C.

According to one preferred embodiment, the keratin fibres are heated in the closed space for a time ranging from 1 s to 60 min, preferably from 5 to 60 s and even more preferentially from 5 to 20 s.

Advantageously, the closed space is kept closed throughout the heating period, i.e. the mobile elements are returned to their open position only when the heating is complete, i.e., in practice, when the heating is switched off. The two mobile elements may then be moved into their open position before or after cooling the device.

Generally, the heating time depends on the set temperature and on the amount of lock introduced into the device.

Advantageously, the locks of hair are inserted into the device without being placed under mechanical tension beforehand. They may be inserted loose into the device, without especially being wound onto a curler. It is also possible for them not to be under mechanical tension when they are inside the closed space.

According to one preferred embodiment, a heat-exchange liquid 80, especially water, is added into the space defined by the two mobile elements receiving the keratin fibres, before or after closing the device. This liquid uniformly distributes the heat in the closed space, and especially on the locks. It also allows increase of the excess pressure generated inside the closed space 20 during the heating.

The process optionally comprises a step of smoothing the keratin fibres, especially after the heating step.

The process then optionally comprises a step of rinsing or washing the keratin fibres after the heating step, generally with water or with shampoo, optionally followed by a drying step and optionally a styling step.

The device 10 used in the treatment process of the invention is described schematically in FIG. 1 in the open position and in partial cross section in the closed position in FIG. 2.

The device comprises two elements 11 and 12 that are mutually mobile between an open position and a closed position in which the two elements 11 and 12 define a closed space 20. The volume of this closed space allows all or part of the head of hair to be placed in this space. Preferentially, the closed space 20 is a flat chamber into which one or more locks M may be introduced.

According to one variant, not shown, a pipe for feeding heat-exchange liquid into the device may be provided in order to add a heat-exchange liquid into the space 20 in the closed position.

In the illustrated example, the two mobile elements are articulated about each other. As a variant, it may be arranged for the two mobile elements not to be articulated, and to be configured so as to fix onto each other in the closed position in order to define the substantially leaktight closed space.

According to the invention, the device 10 comprises a heating means 30. The heating means may be included either in only one of the mobile elements, or in both. Preferably, the heating means is included in both the mobile elements.

The heating means is chosen from a thermal resistance, a source of infrared radiation, a source of microwave radiation, a laser and a source of intense pulsed light. It is preferentially a thermal resistance. The thermal resistance is powered by a battery or by a mains connection.

This heating means is regulated as a function of the temperature desired on the hair. Preferably, the heating means is adjusted so that the temperature detected on the hair is between 40 and 250° C. and preferentially between 70 and 150° C. Preferably, the temperature is measured at standard atmospheric pressure, equal to 101 325 Pa.

Each mobile element comprises an outer shell 40 made, for example, of a thermoplastic material, especially of ABS (acrylonitrile-butadiene-styrene).

The two mobile elements may be heat-insulating, such that throughout the heating period they act as an oven, i.e. the heat is not dissipated outside the device. The temperature is thus kept constant throughout the heating step.

To this end, each mobile element comprises a coating 50 made of a thermally insulating material between the heating means 30 and the outer shell 40. The term "thermally insulating material" means materials with an electrical conductivity of between 0 and 1 W/m.° C. (PVC: 0.17 W/m.° C.).

Advantageously, a plate 60 made of a heat-conducting material covers the thermal resistance and delimits the space 20 so as to homogeneously distribute the heat generated by the thermal resistance in the closed space 20. According to one particular example, the plate is made of aluminium.

The two mobile elements 11 and 12 are designed such that the closed space 20 created is as hermetic as possible. To this end, at least one of the two mobile elements comprises a seal 70 at least partly delimiting the periphery of the closed space.

Preferably, each mobile element comprises a seal 70 delimiting the periphery of the closed space, the seals of the mobile elements being applied against each other in the closed position.

The seal may especially be made of silicone or rubber, perfluorinated elastomer, polyurethane or nitrile.

The two mobile elements of the device are thus leaktight, especially to water and to the applied composition, such that, throughout the heating period, the composition and, where appropriate, the heat-exchange liquid do not escape from the device.

This makes it possible, firstly, to create a confined medium which, by evaporation of the formula, creates a slight excess pressure and, secondly, to avoid running of the cosmetic product applied beforehand to the head of hair.

EXAMPLES

The following rinse-out care compositions were prepared (mass %):

| Composition | Composition 1 | Composition 2 | Composition 3 |
|---|---|---|---|
| cetylstearyl alcohol (C16/C18 50/50) | 5 | 5 | 5 |
| Myristyl/cetyl/stearyl myristate/palmitate/stearate mixture | 1 | 1 | 1 |
| Behenyltrimethylammonium chloride (melting point: 77-80° C.) | 0.79 | 0.79 | 2.96 |
| Isopropyl myristate | 1.05 | 1.05 | 1.05 |
| Ozokerite (melting point: 73-80° C.) | — | 2 | — |
| Isopropyl alcohol | 0.18 | 0.18 | 0.675 |
| Mineral oil | — | — | 0.21 |
| Polyquaternium-37* | — | — | 0.3 |
| Dimethicone | — | — | 0.4 |
| Amodimethicone | — | — | 0.1 |
| Water | qs 100 | qs 100 | qs 100 |

*Crosslinked ethyltrimethylammonium methacrylate chloride homopolymer as an inverse emulsion in a mineral oil Example 1

Invention

Composition 1 was applied to a lock of 2 g of hair. The lock was then placed in the open device 10, and the two mobile elements were then moved into their closed position so as to confine the lock in the space 20. The heating means were then switched on and the lock of hair was heated at 150° C. for 15 s. After this leave-on time, the heating was stopped and, after removing the lock of hair from the device, the said lock was rinsed and then dried in the open air.

Example 2

Reference

Composition 1 was applied to a lock of 2 g of hair for a leave-on time of 5 minutes. The lock was then rinsed and then dried in the open air.

The chosen cationic surfactant (behenyltrimethylammonium chloride), whose melting point is about 80° C., is assayed after application and after shampooing. The initial deposit of cationic surfactant is increased by 12% in the case of Example 1 (input of heat into the confined medium) relative to Example 2. After shampooing, the deposit of surfactant is 10.6 times greater.

Furthermore, the locks were evaluated by a panel of experts, and it emerges therefrom that the locks treated in Example 1 and show greater softness under water and softness on dry hair than the locks treated in Example 2. The coating is more present after application and even after 10 shampoo washes.

The softness of the hair is improved and the remnants of the hair treatment is increased.

Compositions 2 and 3 were also applied and comparative tests with and without input of heat into a confined medium were performed according to the same protocol as for composition 1. The results are the same as for composition 1.

The invention claimed is:

1. A process for treating keratin fibres, the process comprising:
applying a hair treatment composition to the keratin fibres, the hair treatment composition comprising at least one of fatty substances, surfactants, polymers with a glass transition temperature (Tg) ranging from about 40° C. to about 150° C., oxidation dye precursors, or direct dyes;
inserting the treated keratin fibres into a device comprising two rigid elements that are moveable relative to each other between an open position and a closed position, wherein, in the closed position, the two rigid elements define a flat chamber comprising a substantially leaktight closed space;
moving the two rigid elements into the closed position to confine the keratin fibres in the closed space of the flat chamber; and
heating the treated keratin fibres to a temperature ranging from about 40° C. to about 250° C. while the keratin fibres are confined in the closed space of the flat chamber, wherein at least one of the two rigid elements comprises a heat source that generates heat.

2. The process of claim 1, wherein the fatty substances include at least one of fatty alcohols, fatty acids, non-silicone waxes of natural or synthetic origin, and silicone gums.

3. The process of claim 1, wherein the composition comprises at least one compound having a softening point or a melting point ranging from about 40° C. to about 150° C.

4. The process of claim 1, wherein heating the keratin fibres comprises heating the keratin fibres for an amount of time ranging from about 1 second to about 60 minutes.

5. The process of claim 1, wherein heating the keratin fibres comprises heating the keratin fibres for an amount of time ranging from about 5 seconds to about 60 seconds.

6. The process of claim 1, wherein heating the keratin fibres comprises heating the keratin fibres for an amount of time ranging from about 5 seconds to about 20 seconds.

7. The process of claim 1, wherein inserting the keratin fibres into the device comprises inserting loose keratin fibres not wound onto a curler into the device.

8. The process of claim 1, wherein portions of the keratin fibres that are within the closed space are not under mechanical tension.

9. The process of claim 1, further comprising introducing a heat-exchange liquid into the flat chamber defined by the two rigid elements receiving the keratin fibres.

10. The process of claim 9, wherein the heat-exchange liquid comprises water.

11. The process of claim 1, further comprising smoothing the keratin fibres.

12. The process of claim 1, wherein inserting the treated keratin fibres into the device comprises inserting partially dry keratin fibres into the device.

13. The process of claim 1, further comprising rinsing the keratin fibres after heating the keratin fibres.

14. The process of claim 1, wherein each of the two rigid elements comprises a heat source.

15. The process of claim 1, wherein the heat source is chosen from a thermal resistance, a source of infrared radiation, a source of microwave radiation, a laser, or a source of intense pulse light.

16. The process of claim 1, wherein the device comprises at least one seal at least partly delimiting the closed space.

17. The process of claim 1, wherein the device is configured with a seal at least partly delimiting the flat chamber on each of the two rigid elements, wherein the seals are applied against each other in the closed position of the rigid elements.

18. The process of claim 1, wherein the two rigid elements are articulatable relative to each other.

19. The process of claim 1, wherein applying the hair treatment composition to the keratin fibres comprises applying the hair treatment composition to human keratin fibres.

20. The process of claim 19, wherein applying the hair treatment composition to the human keratin fibres comprises applying the hair treatment composition to human hair.

* * * * *